(12) United States Patent
Garios

(10) Patent No.: US 9,975,783 B2
(45) Date of Patent: May 22, 2018

(54) APPARATUS TO CLASSIFY AND SEPARATE TURBID WATER AND CLEAN WATER

(71) Applicant: Wadih Antonio Garios, Juiz de Fora (BR)

(72) Inventor: Wadih Antonio Garios, Juiz de Fora (BR)

( * ) Notice: Subject to any disclaimer, the term of this patent is extended or adjusted under 35 U.S.C. 154(b) by 58 days.

(21) Appl. No.: 15/229,399

(22) Filed: Aug. 5, 2016

(65) Prior Publication Data

US 2017/0088437 A1 Mar. 30, 2017

Related U.S. Application Data

(63) Continuation-in-part of application No. 13/881,708, filed as application No. PCT/BR2011/000407 on Nov. 1, 2011, now abandoned.

(51) Int. Cl.

| C02F 1/76 | (2006.01) |
|---|---|
| C02F 1/68 | (2006.01) |
| G01N 21/59 | (2006.01) |
| C02F 1/00 | (2006.01) |
| E03B 1/04 | (2006.01) |

(Continued)

(52) U.S. Cl.
CPC .............. *C02F 1/004* (2013.01); *C02F 1/008* (2013.01); *C02F 1/685* (2013.01); *C02F 1/76* (2013.01); *E03B 1/041* (2013.01); *E03B 3/02* (2013.01); *C02F 2103/001* (2013.01); *C02F 2103/007* (2013.01); *C02F 2209/11* (2013.01); *C02F 2209/42* (2013.01); *E03B 2001/047* (2013.01); *G01N 21/59* (2013.01)

(58) Field of Classification Search
CPC .......... C02F 1/004; C02F 1/008; C02F 1/685; C02F 1/76; C02F 2103/001; C02F 2103/007; C02F 2209/11; C02F 2209/42; E03B 1/041; E03B 2001/047; E03B 3/02; G01N 21/59

See application file for complete search history.

(56) References Cited

U.S. PATENT DOCUMENTS 2,463,814 A * 3/1949 Skinner .................... D21F 1/66
210/232
5,114,594 A * 5/1992 Rosebrock .............. E04D 13/08
137/357

(Continued)

FOREIGN PATENT DOCUMENTS

| JP | 07207714 A | * | 8/1995 | |
| WO | WO-2010075617 A1 | * | 7/2010 | .............. C02F 1/006 |

*Primary Examiner* — Terry K Cecil
(74) *Attorney, Agent, or Firm* — Nevrivy Patent Law Group P.L.L.C.

(57) ABSTRACT

An apparatus to classify and separate turbid water and clean water water is disclosed, basically comprising a turbidity metering section which measures the turbidity of a flow of water based on the absorption of a beam of light in the flow of water and in the measurement of the electrical conductivity of the flow of water, and a turbid water separation section comprising a deviation device having an external body and an internal deviator, the external body being provided with a turbid water outlet connected to a discard outlet, which discards turbid water, and a clean water outlet connected to a clean water transfer pipe, which transfers clean water to a clean water tank.

18 Claims, 5 Drawing Sheets

(51) Int. Cl.
*E03B 3/02* (2006.01)
*C02F 103/00* (2006.01)

(56) References Cited

U.S. PATENT DOCUMENTS

| | | | | |
|---|---|---|---|---|
| 6,077,423 A * | 6/2000 | Roy | ................... | B01D 29/15 |
| | | | | 210/121 |
| 6,884,001 B1 * | 4/2005 | Dunn | ................... | E02B 3/02 |
| | | | | 210/745 |
| 7,550,077 B2 * | 6/2009 | Graf | ................... | E03B 3/02 |
| | | | | 210/162 |
| 8,033,058 B2 * | 10/2011 | Block | ................... | E04D 13/08 |
| | | | | 210/162 |
| 9,206,321 B2 * | 12/2015 | Yamaguchi | ............ | C23C 22/53 |

* cited by examiner

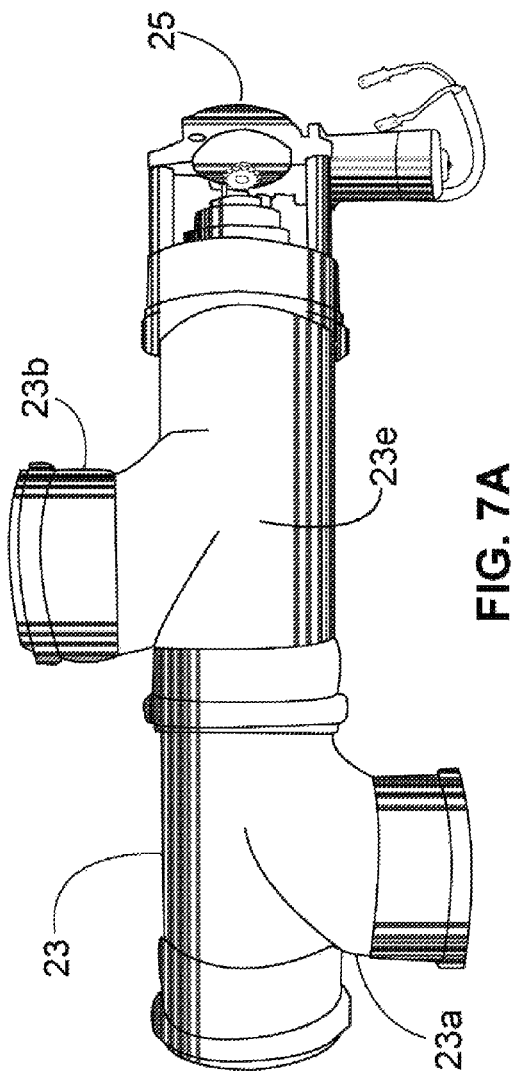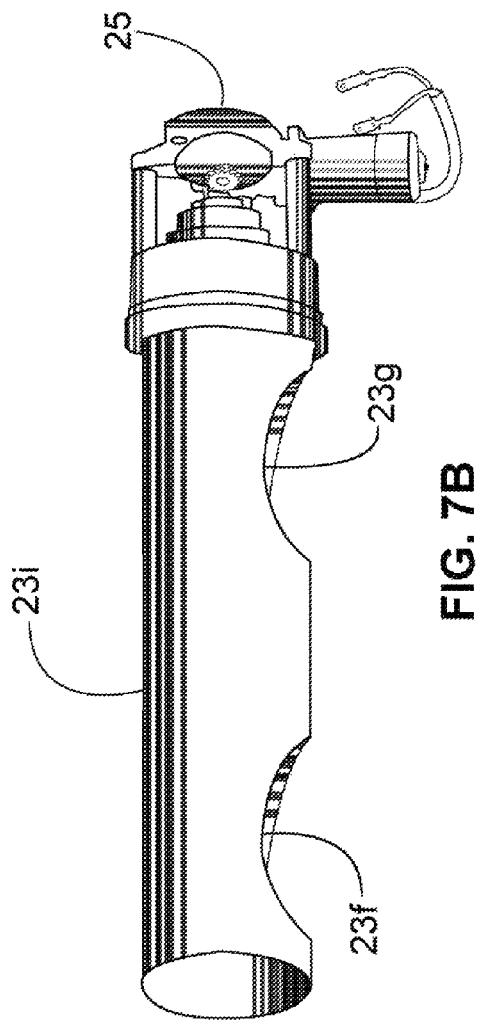
FIG. 7A
FIG. 7B

APPARATUS TO CLASSIFY AND SEPARATE TURBID WATER AND CLEAN WATER

CROSS-REFERENCE TO RELATED APPLICATIONS

This application is a continuation-in-part of U.S. application Ser. No. 13/881,708, which is the U.S. National Stage of International Application No.: PCT/BR2011/00407, filed Nov. 1, 2011. The content of the aforementioned applications are relied upon and is incorporated by reference in its entireties.

FIELD OF THE INVENTION

The present invention refers to an apparatus to classify and separate turbid water and clean water, such as flows of water from rainfalls, rivers, lakes, ponds and the like.

RELATED ART

Frequently it is necessary to classify and separate turbid water which is collected from a number of sources, such as turbid rainwater, water collected in rivers, ponds and lakes, etc.

As regards rainwater, there are, at present, various processes to collect and use rainfall turbid water. The simplest of them consist of the rainwater being collected directly into a cistern, and in others the first flow of rainwater is manually deviated until it seems clean to an operator. Next the flow of rainwater is redirected to a cistern. U.S. Pat. No. 6,077,423A, U.S. Pat. No. 6,884,001B1, JP07-207,714A disclose some processes and devices to collect rainwater.

JP07-207,714A discloses a system to eliminate turbidity of collected rainwater. It is described a system for collecting rainwater that comes directly from roofs. However, it is not disclosed a system to eliminate rubbish contained in the flow of rainwater, thereby making it an incomplete process to eliminate turbidity of rainwater.

Contamination of the collected rainwater may arise as it is temporarily stored in an intermediate reservoir meanwhile the turbidity is measured, and volumes of processed rainwater from different steps of the process are directed to this reservoir, whereby more rainwater may contaminate the whole volume of water in this reservoir.

Another drawback of JP07-207,714A is the use of PH measurement, using electrodes, to infer the turbidity of the water. This is a non-precise method to measure turbidity. The presence of dust, pollution, debris or any material in suspension may cause errors in the turbidity measurement thereby making difficult to determine the turbidity of the water accordingly.

Further, when the rain ceases, a decantation process starts, and then a layer of mud forms on the bottom of this intermediate reservoir, where the measurement of the turbidity is done. This is inadequate, as with time going by, a still and apparently clean water region will form in the top of the reservoir, though it is still contaminated by suspended micro contaminants not decanted on the lower layer of mud, and this may cause a false measurement of less turbidity of the whole volume of the water in the reservoir.

Consequently, there is a risk, when a following rainfall occurs, that this still and apparently less turbid water is outflowed to the end reservoir, creating risk of contamination of the whole volume of water contained in this end reservoir and making it inappropriate for use.

U.S. Pat. No. 6,884,001B1 discloses a process used for another purpose, in rivers that flow into lakes, to avoid silting. There is no precision in the turbidity measurement. Further, there is not a filter located upstream of the turbidity meter to eliminate leaves, branches and other debris from flowing through, which causes difficult for the measuring process and may hinder the closing of the water flow diverting doors.

Furthermore, there is not a possibility for an auto calibration in the process between the signals of the beam of light and the receptor of luminosity to compensate the presence of particulate material in the water, thereby harming the quality of the water. The water resultant of this process is not appropriate for human use in general.

U.S. Pat. No. 6,077,423A discloses a method and a system for collecting and treating rainwater runoff in decanting basins and allowing the runoff to settle in the basin for a predetermined time before allowing the filtration step to be initiated. The filtration system comprises a plurality of filtration canisters containing replaceable filter media or cartridges plumbed to a common drain pipe is controlled by an automated shut-off valve activated by an electronic controller.

Filtration and separation of storm rainwater begin after sedimentation has occurred over a specified period of time and/or when the turbidity of storm rainwater being held for filtration has been reduced to a specified level. An electronic controller monitors environmental conditions and the conditions of the storm rainwater being held for filtration. The controller opens and closes the automated shut-off valve as necessary to allow separation and filtration. It's a very complex and high cost system, with a variety of interlinked mechanisms, prone to flaws, rendering it difficult for the population to use the process to obtain clean water.

All the documents mentioned above disclose processes and/or systems having drawbacks, besides being expensive if used to collect and to treat turbid water in order to guarantee water free from contamination. Auxiliary systems are not provided in the beginning of the disclosed processes, such as a separating filter and debris/rubbish remover to remove debris and rubbish and to filter the turbid water coming from the collecting system, which would prevent debris and rubbish from interfering with the measurement of the turbidity of the water. If rubbish and debris are present they may cause contamination in the treated water.

Further, these systems are not provided with means to calibrate the turbidity measuring device to compensate contingent dirty that may form in the reading device in view of the presence of particulate material in the collected turbid water, which may cause mismeasurement of turbidity, thereby enabling the acceptance by the systems of nonstandard water.

The apparatus and method to classify and separate turbid water object of the present invention was developed to address the above mentioned problems.

SUMMARY OF THE INVENTION

In a first aspect the invention relates to an apparatus to classify and separate turbid water and clean water in a flow of water, the apparatus including a water passage sensor installed in a feeding pipe which supplies turbid water to the apparatus; a first descending/ascending pipage, comprising a first downward pipe, a first intermediate pipe and a first upward pipe; a turbidity metering section provided with first and second transparent windows respectively located at opposite first and second ends of the turbidity metering section, a light beam emitter located in front of the first transparent window, a light beam sensor located in front of the opposite second transparent window; a second descending/ascending pipage, comprising a second descending pipe, a second intermediate pipe and a second ascending pipe; a turbid water separation section comprising a deviation device having an external body, an internal deviator and an actuating device, the external body being provided with a turbid water outlet connected to a discard outlet and a clean water outlet connected to a clean water transfer pipe which transfers clean water to a clean water tank, the internal deviator being provided with a first deviation outlet and a second deviation outlet, both being downwardly oriented in a default position in which the first deviation outlet is aligned with the turbid water outlet, and the second deviation outlet is blocked, the internal deviator being able to turn within the external body, driven by the actuating device; a control module provided with a data bank containing information on the correlation of water turbidity and light absorption for the source of light being used, the control module being able to receive signals from the water passage sensor in order to command the light beam emitter, the control module being able to receive signals from the light beam sensor to command the actuating device; and further the control module is provided with a signalization panel to indicate the status of the whole operation of the apparatus to classify and separate turbid water and clean water.

A receiving reservoir may be used to receive the flow of turbid water via a supply pipe, the receiving reservoir being provided with an air vent and a receiving reservoir outlet, which is connected to the feeding pipe. The use of the receiving reservoir enables most of the air entrained in the flow or turbid water to be vented via the air vent.

Further, an air release device may be installed upstream of the first downward pipe of the first descending/ascending pipage. Furthermore, first and second air vents may be installed in the turbidity metering section near the first and second ends, respectively.

First drain and second drain located upstream of and downstream of the turbidity metering section, respectively, may also be provided, having respectively first blocking valve and second blocking valve and serving to drain and dry the turbidity metering section when the apparatus to classify and separate turbid water and clean water is not in use.

Moreover, a chlorinator may be provided in the clean water transfer pipe upstream of the clean water tank.

A level sensor may be provided in the clean water tank to sense high level of clean water in the clean water tank and to send a signal to the control module in order to cause drainage of the excess of clean water in the clean water tank.

The clean water tank may be provided with a draining device which discards the excess of water via a releasing outlet.

Additionally, a third blocking valve may be provided in the supply pipe, installed downstream of a discarding deviation, the latter being provided with a fourth blocking valve.

Further, an acoustic device may be provided, which receives a command signal from the control module when at least one of the components is malfunctioning and then emits sound signals to inform such an occurrence.

Yet it may be provided a no-break device having an internal rechargeable battery, the no-brake device being able to sense an outage of the power supply in the circuit and then to supply power to the parts that consume power, the internal rechargeable battery of the no-brake being connected to the electric network in order to be permanently fully charged.

In a second aspect the invention relates to a method to classify and separate turbid water and clean water comprising the steps of:

allow a flow of turbid water to pass through a feeding pipe; allow a water passage sensor to sense the passage of said flow of turbid water in the feeding pipe and to send a signal to a control module informing the passage of said flow of turbid water;

allow the control module to send a command signal to a light beam emitter located in front of a first transparent window of a turbidity metering section to start beaming light;

next allow the flow of turbid water to enter a first descending/ascending pipage, flowing first through a first downward pipe, then through a first intermediate pipe and next through a first upward pipe;

allow the flow of turbid water to pass through a turbidity metering section provided with first and second transparent windows located at opposite first and second ends of the turbidity metering section, said light beam emitter located in front of the first transparent window, and a light beam sensor located in front of the opposite second transparent window;

allow the light beam sensor located in front of the opposite second window to sense said beam of light and to send a signal to the control module;

next allow the flow of turbid water to pass through a second descending/ascending pipage, flowing first through a second descending pipe, then through a second intermediate pipe and next through a second ascending pipe;

allow the flow of turbid water to pass through a turbid water separation section comprising a deviation device provided with an actuating device, the deviation device comprising an external body and an internal deviator, the external body being provided with a turbid water outlet connected to a discard outlet, and a clean water outlet connected to a clean water transfer pipe, the internal deviator being provided with a first deviation outlet and a second deviation outlet, both being downwardly oriented in a default position, in which the first deviation outlet is aligned with the turbid water outlet, and the second deviation outlet is blocked, the internal deviator being able to turn within the external body, driven by the actuating device;

allow the initial flow of turbid water to flow through the first deviation outlet, the turbid water outlet and the discard outlet, to be discarded;

allow the control module to analyze and to automatically classify and separate the flow of passing turbid water based on the signals received from the light beam sensor, thereby accepting or rejecting the passing flow of water that do not match the desired standards;

whenever the control module decides that the passing flow of water meets the desired standards, then it sends a command signal to the actuating device of the deviation device to rotate the internal deviator so as to enable the second deviation outlet to align with the clean water outlet, causing the passing flow of clean water to pass through the clean water transfer pipe towards a clean water tank.

Further, the signals received from the water passage sensor are also considered in the step wherein the control module analyzes and to automatically classifies and separate the passing flow of water based on the signals received from the light beam sensor.

Furthermore, the method may also comprise the step of chlorinating the flow of clean water in a chlorinator before it is stored in the clean water tank.

In addition the method may include the step of sensing high level of clean water in the clean water tank, via a level sensor that sends a signal to the control module, which sends a command signal to a draining device to discard the excess of water via a releasing outlet.

Yet the method may include a step of the control module sending a command signal to a third blocking valve provided in one among the supply pipe and the feeding pipe to shut off and to a fourth blocking valve to open, said fourth blocking valve installed in a discarding deviation located upstream of said third blocking valve, thereby making the flow of turbid water to be discarded, the control module also sending a command signal to the light beam emitter to stop emitting light signals, in order to save electric power.

Moreover the method may include the step of allowing the level sensor to keep sensing the clean water level into the clean water tank and whenever it senses that said level reduces to a pre-established level, then the level sensor sends a signal to the control module, which sends a command signal to the draining device to close and also sends a command signal to the third blocking valve to open and to the fourth blocking valve to shut off, and further the command module sends a command signal to the light beam emitter to send again light signals to the light beam sensor.

BRIEF DESCRIPTION OF THE DRAWINGS

The invention will be better understood through the following detailed description in accordance to the attached drawings, wherein:

FIGS. 7A and 7B are schematic views of a deviation valve of the apparatus to classify and separate turbid water and clean water object of the present invention.

DETAILED DESCRIPTION OF THE INVENTION

When turbid water from a rainfall, a river, a pond, a lake, etc. is collected for industrial, agricultural or home uses, it is first necessary to remove huge materials like leaves, branches and rubbish in general, coming from the collecting areas from the collected turbid water. Further, it is also necessary to filter the flow of turbid water to separate sand, dust, pollution, debris or any material in suspension.

These steps are important for the safe operation of the apparatus to classify and separate turbid water and clean water object of the present invention, as the presence of these contaminants in the flow of turbid water that passes through the apparatus would cause difficulties for a precise measurement of the turbidity of a flow of water.

Figure 3:
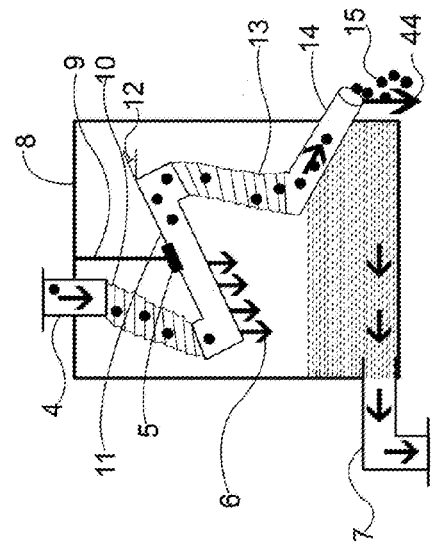
FIGS. 1, 2 and 3 depict a filtering device which may be used together with the apparatus to classify and separate turbid water and clean water object of the present invention.
Figure 2:
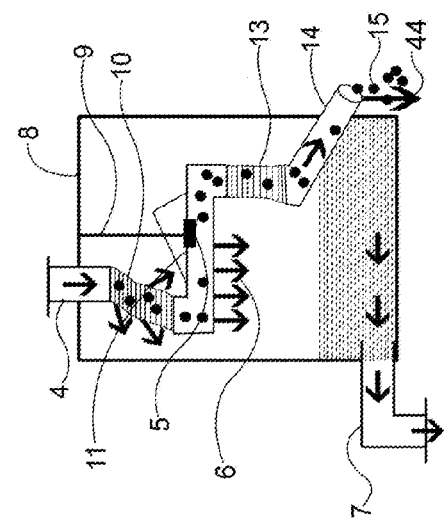
Figure 1:
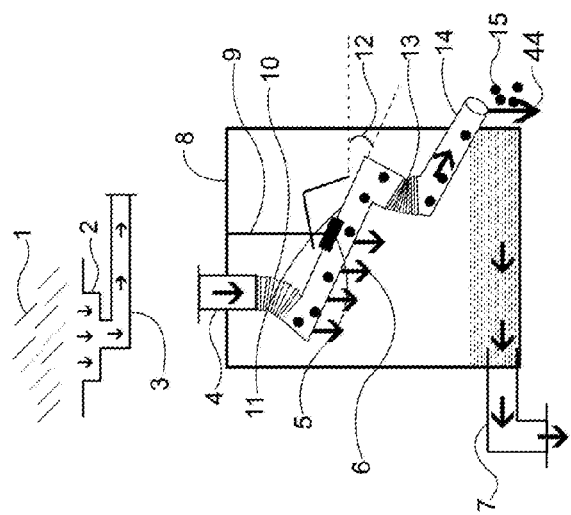

FIGS. 1, 2, 3 depict a filtering device which may be used together with the apparatus to classify and separate turbid water and clean water object of the present invention, when it is used to classify and separate turbid rainwater. It is described in more details in the commonly owned U.S. Pat. No. 9,260,321, the content of which is herein incorporated by reference. Turbid water 1 is collected in collecting devices 2, and the collected turbid water is carried to the filtering device by means of a connecting pipe 3.

Although the filtering device depicted in FIGS. 1, 2, 3 is not part of the present invention, it will be done a brief description of its functional features, as the pre-filtration of turbid water is important for the perfect operation of the system.

It is important to mention that any filtering device able to filter turbid water may be used, and the following description is made for the sake of exemplification only. The turbid rainwater flow, which may contain dust, sand and rubbish in general, enters the filtering device via a rainwater inlet 4 and passes through a filter assembly comprising first 10, second 11 and third 13 filter elements, preferably being tubular in shape.

The walls of the first 10, second 11 and third 13 filter elements are preferably made of screen mesh and are able to expand or retract to adapt to the flowrate of turbid water, in order to eliminate rubbish 15 and the like which had entered the filter elements of the filtering device.

A tilting calibrator 5 is provided in the upper part of the second filter element 11, and is pivotally connected to an end of a rod 9. The other end of the rod 9 is pivotally connected to the upper part of the filtering device. The assembly formed by the tilting calibrator 5, rod 9 and the first, second and third filter elements (10, 11, 13) is designed to adapt to the flowrate of rainwater, according to its calibration.

During periods of downpour, or sudden rain, the second filter element 11, which is attached to the rod 9, adapts its position according to the rainwater flow and changes its inclination. Therefore the first 10 and third 13 filter elements expand, thereby increasing their area for filtering rainwater in order to filter the maximum possible volume of rainwater.

Rainwater 6 from the first 10, second 11 and third 13 filter elements is poured downward in the filtering device reservoir and is drained out from it via a filter outlet 7.

The initial position of the first 10, second 11 and third 13 filters elements is calculated to facilitate expulsion of rubbish 15 from the filtering device via a rubbish outlet 14. They have a steeper inclination when there is a weak rainfall, which allows the exit of rubbish 15 (FIG. 1). This position changes in proportion with the increase of the rain, changing to the position depicted in FIG. 2, and may gradually reach the position depicted in FIG. 3, as a function of the flow of rainwater.

When the flow of rainwater reduces, the second filter element 11 begins to return to its initial programmed position, and the first 10 and third 13 filter elements begin to retract proportionally, increasing the angle of inclination 12 of the second filter element 12. Consequently rubbish 15 is discarded through the rubbish outlet 14, carrying a very small volume of discarded water 50 (FIG. 1).

Even when the filter assembly is inclined, as depicted in FIG. 3 (a condition of heavy downpour), all the rubbish will be expelled from the filter assembly. The tilting orientation of the second filter element 11, connected to the rod 9, will always be a function of the flowrate of rainwater.

The shape and the mobility of the first 10, second 11 and third 13 filtering elements, as well as the feature that they have permeable walls, enable them to filter higher volumes of rainwater, even if it occurs abrupt changes in the flowrate of the rainfall, if compared to the existing rainwater filters, which squander a higher volume of rainwater.

Furthermore, as rubbish is totally expelled from the first 10, second 11 and third 13 filter elements, the filtering device maintains its capacity to filter rainwater for longer periods of time.

It is important to mention that the above description of the filtering device of U.S. Pat. No. 9,260,321 was made for the sake of exemplification only, as any kind of turbid water filtering device may be used.

In the cases in that turbid water is collected in rivers, lakes, ponds, etc., it is also necessary to remove huge materials like leaves, branches and sized rubbish in general, as well as to filter the flow of turbid water to separate sand, dust, pollution, debris or any material in suspension, which are important steps for the safe operation of the apparatus to classify and separate turbid water and clean water object of the present invention.

It will be apparent from the following description of the invention.

Immediately after a downpour storm stars, the first turbid water collected in the collecting areas come to the filtering device containing sized rubbish and also contaminants such as dirt, dust, particulate matter suspended in the atmosphere which is carried to the ground by the raindrops, etc., The majority of them is filtered and discarded by filtering devices, but in the first moments of the downpour it is possible that part of the fine particulate material may survive filtration, and is important to avoid the use of water containing these pollutants.

Similarly, when water is collected in rivers, lakes, ponds, etc., the flow of collected water usually comes with such sized rubbish and also contaminants such as dirt, dust, particulate matter, which may be eliminated by decantation and filtering processes. Nevertheless, likewise in the case of the use of rainwater, is possible that part of the fine particulate material may survive filtration, and is important to avoid the use of water containing these pollutants.

Figure 4:
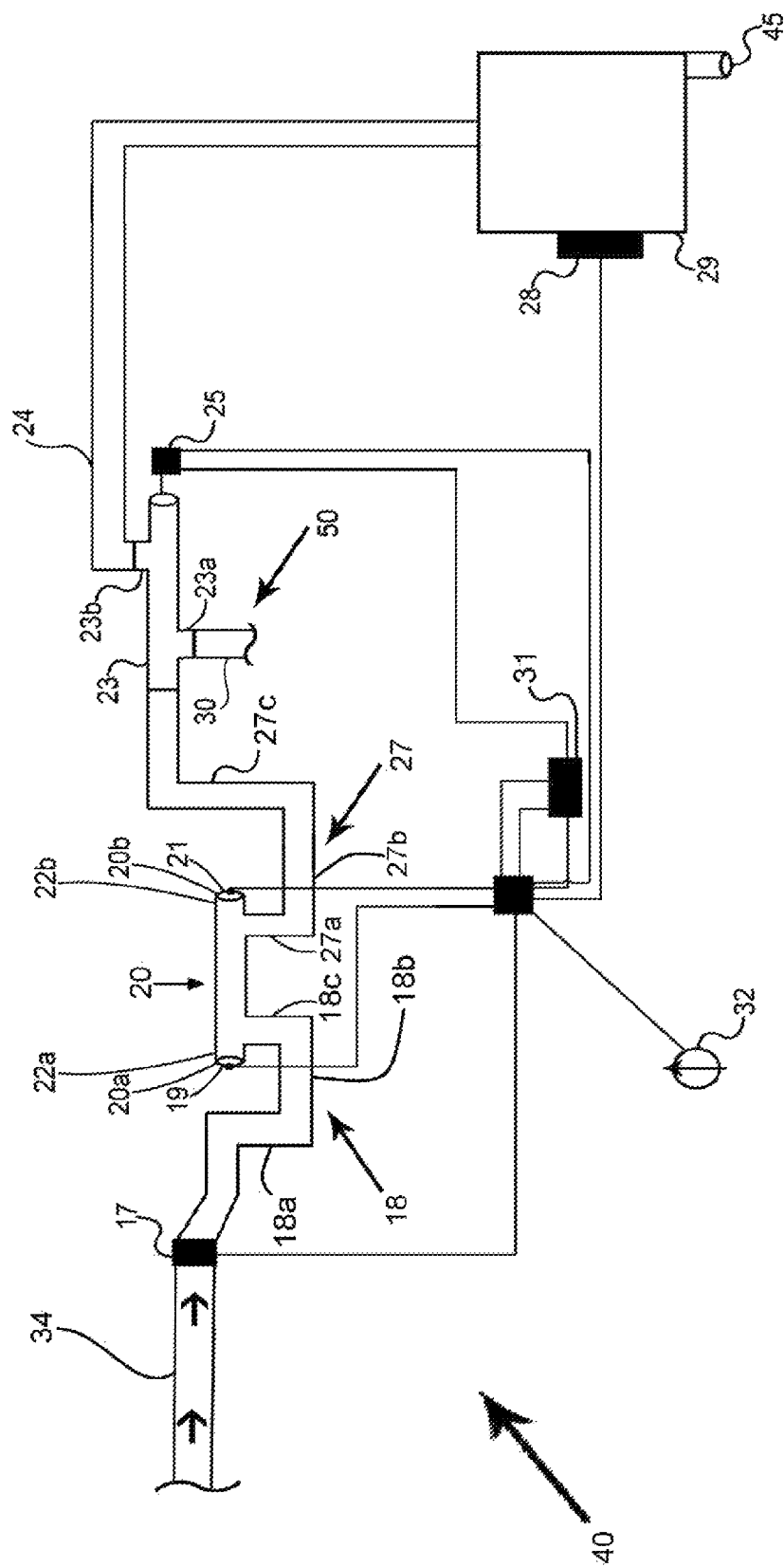
FIG. 4 is a schematic view of the apparatus to classify and separate turbid water and clean water object of the present invention.

FIG. 4 depicts an apparatus to classify and separate turbid water and clean water 40, object of the present invention, which enables to classify and separate turbid water and clean water from clean water.

A feeding pipe 34 receives a flow of water, preferably coming from a turbid water filtering device, the flow being directed to the apparatus to classify and separate turbid water and clean water 40, passing initially through a passage sensor 17, which is a device that senses and measures the instant electrical conductivity of the passing flow of water and sends a command signal to a control module 33, informing the passage and the instant electrical conductivity of the passing flow of water.

The control module 33 is programmed to do an auto calibration, which could be done at the moment the water passage sensor 17 detects the passage of water through the feeding pipe 34.

The measurement of the electrical conductivity, as well as the measurement of turbidity are both useful to determine the turbidity of the passing flow of water, as will be seen in the following description.

After passing through the water passage sensor 17 the flow of water passes through a first descending/ascending pipage 18, flowing first through a first downward pipe 18a, then through a first intermediate pipe 18b and next through a first upward pipe 18c, entering then a turbidity metering section 20.

Figure 6:
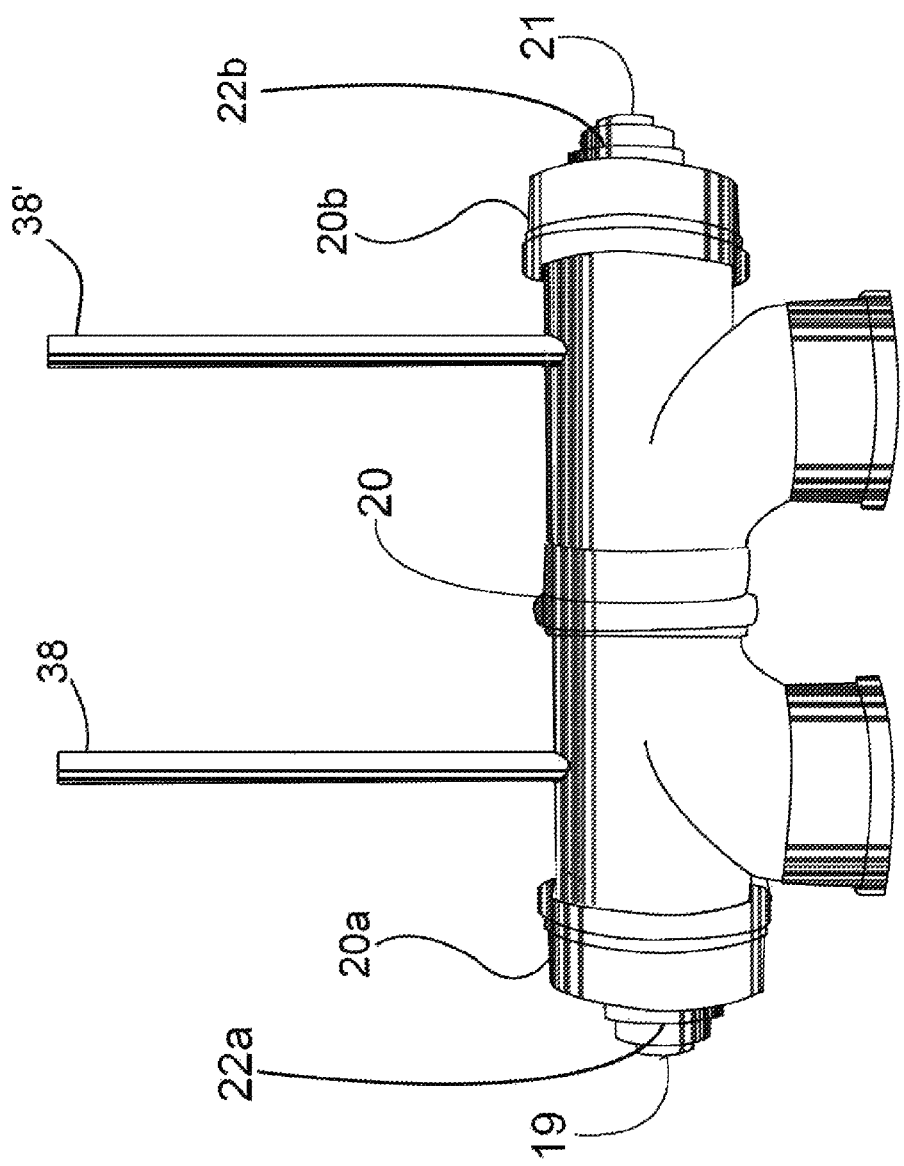
FIG. 6 is a schematic view of a turbidity measurement section of the apparatus to classify and separate turbid water and clean water object of the present invention.

As can be better seen in FIG. 6, first and second windows (22a, 22b), which are transparent and have means to prevent formation of mist and water droplets on its transparent surfaces, such as a heating system, are respectively located at opposite first end 20a and second end 20b of the turbidity metering section 20.

A light beam emitter 19 is located in front of the first window 22a. A light beam sensor 21 is located in front of the opposite second window 22b. The assembly of the light beam emitter 19/first window/22a and the assembly of the light beam sensor 21/second window 22b are external-light-proof in order to preclude interferences from external light in the operation of both the light beam emitter 19 and the light beam sensor 21.

Immediately after the control module 33 receives a signal from the water passage sensor 17, informing the passage of a flow of water, it emits a command signal to the light beam emitter 19, which then starts sending light signals to the light beam sensor 21. The light beam emitter 19 is normally off in idle time, in order to save energy when there is not a passage of water in the apparatus to classify and separate turbid water and clean water object of the present invention.

The light beam sensor 21 permanently sends signals to the control module 33 informing the intensity of the light signal received from the light beam emitter 19. The signal of light that reaches the light beam sensor 21 serves as a reference against the signal of light coming from the light beam emitter 19.

The more turbid is the water, the more light absorption will occur in the flow of water flowing into the turbidity metering section 20. Conversely, the less turbid is the passing flow of water into the turbidity metering section 20, the high is the intensity of the light signal received by the light beam sensor 21.

After passing through the turbidity metering section 20 the flow of water passes through a second descending/ascending pipage 27, flowing first through a second descending pipe 27a, then through a second intermediate pipe 27b and next through a second ascending pipe 27c, entering then a turbid water separation section 50, which comprises a deviation device 23 provided with an actuating device 25. The turbid water separation section 50 is shown in more details in FIGS. 7A and 7B.

As can be seen in FIG. 7A, the deviation device 23 comprises an external body 23e and an internal deviator 23i.

The external body 23e is provided with a turbid water outlet 23a, which is connected to a discard outlet 30, through which a flow of turbid water is discarded, e.g. to a sewerage system. The external body 23e is also provided with a clean water outlet 23b, which is connected to a clean water transfer pipe 24, through which the flow of clean water is directed to a clean water tank 29.

The internal deviator 23i, which is depicted in FIG. 7B, is installed inside the external body 23e and is able to turn within the external body 23e, driven by the actuating device 25.

The internal deviator 23i is provided with a first deviation outlet 23f and a second deviation outlet 23g, both being downwardly oriented in a default position, in which the first deviation outlet 23f is aligned with the turbid water outlet 23a, and the second deviation outlet 23g is blocked.

The control module 33 is provided with a data bank containing information on the correlation of water turbidity and light absorption for the source of light being used, as well as information on water turbidity and electrical conductivity.

Therefore, based on pre-loaded standards of electrical conductivity and light absorption to measure turbidity, it is programmed to automatically classify and separate the flow of passing water, accepting or rejecting water that do not match the desired standards of turbidity.

Mainly the turbidity of the flow of water is measured by using data coming from the turbidity metering section 20, wherein light absorption is used to determine turbidity. But it is also possible to make a correlation between the results obtained in the turbidity metering section 20 and the electrical conductivity of the flow of water measured by the water passage sensor 17, in order to achieve more precise results for metering turbidity.

Therefore, using these standards, the control module 33 classifies the passing flow of water and, depending on the results of the measurement of the turbidity of the passing flow of water, the control module 33 decides if such passing flow of water is classified as clean water or as turbid water.

As the initial flow of water may contain dust, suspended particulate material and the like, and as in the default position first deviation outlet 23*f* is in alignment with the turbid water outlet 23*a*, consequently this initially turbid flow of water is discarded through the turbid water outlet 23*a* and the discard outlet 30.

Whenever the control module decides that the turbidity of the passing flow of water meets the standards for classifying it as clean water, then it sends a command signal to the actuating device 25 to rotate the internal deviator 23*i*, thereby blocking the first deviation outlet 23*f* and enabling the second deviation outlet 23*g* to align with the clean water outlet 23*b*, causing then the flow of clean water to pass through the clean water transfer pipe 24 towards the clean water tank 29.

Therefore, filtered and clean water is stored in the clean water tank 29 and may be distributed to end uses by a clean water tank outlet 45.

The control module 33 is provided with a signalization panel, not shown in the Figures, to indicate the status of the whole operation of the apparatus to collect, classify and separate turbid water and clean water 40. Furthermore, it is also provided an acoustic device 35 which receives a command signal from the control module 33 when al least of one of the components is malfunctioning and then emits sound signals to inform such an occurrence.

An electric network 32 provides the supply of electric power to the control module 33 and the other parts that require electric energy to operate.

Figure 5:
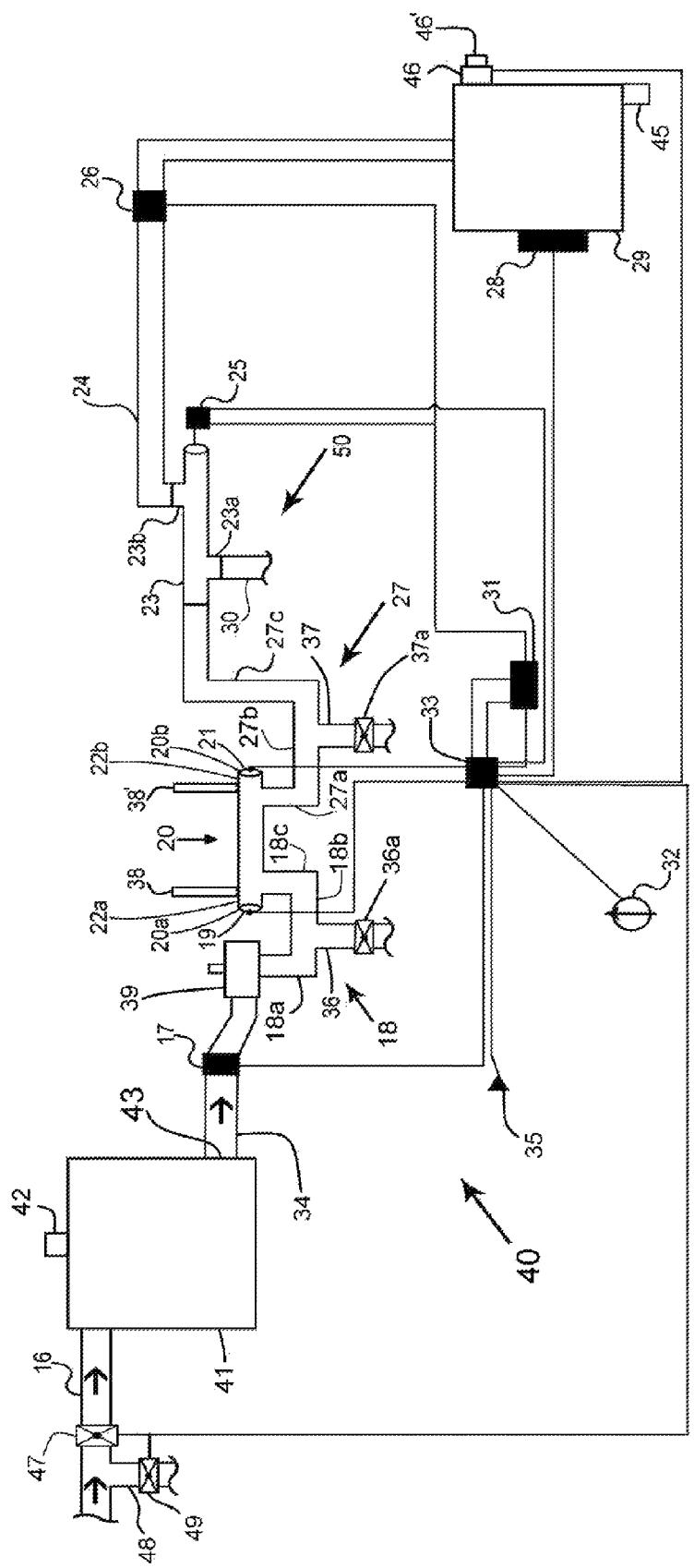
FIG. 5 is a schematic view of the apparatus to classify and separate turbid water and clean water object of the present invention depicted in FIG. 4 provided with some additional components.

FIG. 5 depicts the apparatus to classify and separate turbid water and clean water 40 wherein some improvements have been added, as described in the following.

A supply pipe 16 receives a flow of water, preferably coming from a turbid water filtering device, and this flow is collected in a receiving reservoir 41, provided with a receiving reservoir air vent 42 and a receiving reservoir outlet 43, the latter being connected to the feeding pipe 34, as shown in FIG. 4.

The use of the receiving reservoir 41 enables most of the air bubbles entrained in the flow or turbid water to be vented via the air vent 42. Turbidity is caused by particulate and colored material in water, but it can also be caused by air bubbles entrained in a flow of water. For that reason is important to release the air bubbles.

The flow of water exits the receiving reservoir outlet 43 and passes through the feeding pipe 34, passing next through the water passage sensor 17.

As air bubbles still remaining in the flow of water may cause disturbance in the process of measuring the turbidity of the passing flow of turbid water, an air bubbles release device 39 is provided, e. g. an air valve, installed upstream of the first downward pipe 18*a* the first descending/ascending pipage 18, aiming at eliminating air bubbles in the passing flow of water.

It is also shown in FIG. 5 the provision of first air vent 38 and second air vent 38', installed in the turbidity metering section 20 near the first end 20*a* and the second end 20*b*, respectively, to remove air bubbles that may still remain in the flow of water.

First drain 36 and second drain 37, respectively provided with first blocking valve 36*a* and second blocking valve 37*a*, are located upstream of and downstream of the turbidity metering section 20, respectively, serving to drain and dry the turbidity metering section 20 when the apparatus to classify and separate turbid water and clean water 40 object of the present invention is not in use.

An optional chlorinator 26 may be provided to chlorinate the flow of clean water before it is stored in the clean water tank 29, and in this case the clean water transfer pipe 24 directs the flow of clean water first to the chlorinator 26, before it is directed to the clean water tank 29. The control module 33 is programmed to send command signals to the chlorinator 26 in order to control the addition of chlorine to the passing flow of clean water.

A level sensor 28 may be provided to control the level of the clean water tank 29. In case the level of clean water is high, the level sensor 28 sends a signal to the control module 33, which makes a draining device 46 of the clean water tank 29 to discard the excess of clean water to a sewerage system or the like, via a releasing outlet 46'.

Additionally, a third blocking valve 47 may be provided in the supply pipe 16, installed downstream of a discarding deviation 48, provided with a fourth blocking valve 49, and in case the level sensor sends a signal to the control module 33 informing that the level of clean water in the turbid water tank outlet 45 is high, then the control module 33 sends a command signal to the third blocking valve 47 to shut off and to the fourth blocking valve 49 to open, making the entering flow of water to be discarded.

This operation hinders the unnecessary use of chlorine in the chlorinator 26, as any further volume of chlorinated clean water entering in the clean water tank 29 would be discarded.

Further, in this situation the control module 33 also sends a command signal to the light beam emitter 19 to stop emitting light signals, in order to save electric power.

The third blocking valve 47, the discarding deviation 48 and the fourth blocking valve 49 may be used even if the receiving reservoir 41 is not used. In this case these components would be installed in the feeding pipe 34, instead of in the supply pipe 16.

When the level of clean water in the turbid water tank 29 reduces to a pre-established level, the level sensor 28 sends a command signal to the control module 33, which sends a command signal to the draining device 46 of the clean turbid water 29 to cease discarding clear water.

Further, the control module 33 sends a command signal to the third blocking valve 47 to open and to the fourth blocking valve 49 to shut off, respectively, and also it sends a command signal to the light beam emitter 19 to send again light signals to the light beam sensor 21.

A no-break device 31 is provided, which has an internal rechargeable battery. The no-break device 31 is able to sense a fail in the electric power supply from the electric power supply 32. If it occurs, the internal battery of the no-brake device is able to supply electric power to the system. Therefore, the apparatus to classify and separate turbid water and clean water 40 would operate during a rainfall even if an outage of the power supply occurs.

The internal rechargeable battery of the no-brake device 31 is connected to the electric network 32, in order to remain permanently fully charged.

The connection between the control module 33 and the components it controls may be wired or wireless.

The apparatus to classify and separate turbid water and clean water 40 described heretofore, object of the present invention, provides a safe and easy way to verify the purity and the quality of a flow of water, thereby allowing the classification and separation of the turbid water and clean water in an effective way.

Modifications may be made in the invention without departing from its inventive concept. For example, a laser beam emitter, with a respective laser beam detector, may be used in the turbidity metering section 20 instead of a light beam emitter and a light beam sensor. In this case it would be measured the absorption of the laser beam.

The invention was described herewith with regard to its preferred embodiments, but is not limited to it. Further, although specific technical terms may have been used herein, they were used only in a generic and descriptive form and not to limit the invention, which is only limited by the scope of the following claims.

LIST OF PARTS

1—turbid water
2—collecting device
3—connecting pipe
4—rainwater inlet
5—calibrator
6—turbid water
7—filter outlet
8—descending duct
9—rod
10—first filter element
11—second filter element
12—angle of inclination
13—third filter element
14—rubbish outlet
15—rubbish
16—supply pipe
17—water passage sensor
18—first descending/ascending pipage
18a—first downward pipe
18b—first intermediate pipe
18c—first upward pipe
19—light beam emitter
20—turbidity metering section
20a—first end (of the turbidity metering section)
20b—second end (of the turbidity metering section)
21—light beam sensor
22a—first transparent window
22b—second transparent window
23—deviation device
23a—turbid water outlet
23b—clean water outlet
23e—external body
23f—first deviation outlet
23g—second deviation outlet
23i—internal deviator
24—clean water transfer pipe
25—actuating device
26—chlorinator
27—second descending/ascending pipage
27a—second descending pipe
27b—second intermediate pipe
27c—second ascending pipe
28—level sensor
29—clean water tank
30—discard outlet
31—no-brake device
32—electric network
33—control module
34—feeding pipe
35—acoustic device
36—first drain
36a—first blocking valve
37—second drain
37a—second blocking valve
38—first air vent
38'—second air vent
39—air bubbles release device
40—apparatus to classify and separate turbid water and clean water
41—receiving reservoir
42—receiving reservoir air vent
43—receiving reservoir outlet
44—rubbish
45—clean water tank outlet
46—draining device
46'—releasing outlet
47—third blocking valve
48—discarding deviation
49—fourth blocking valve
50—turbid water separation section

What is claimed is:

1. An apparatus to classify and separate turbid water and clean water coming from a collecting source including:
a feeding pipe provided with a passage sensor;
a first descending/ascending pipage, comprising a first downward pipe connected to a first intermediate pipe, which is connected to a first upward pipe;
a turbidity metering section provided with first and second transparent windows respectively located at opposite first and second ends of the turbidity metering section, a light beam emitter located in front of the first transparent window, a luminosity sensor located in front of the opposite second transparent window;
a second descending/ascending pipage, comprising a second descending pipe connected to a second intermediate pipe, which is connected to a second ascending pipe;
a turbid water separation section comprising a deviation device having an external body, an internal deviator and an actuating device, the external body being provided with a turbid water outlet connected to a discard outlet and a clean water outlet connected to a clean water transfer pipe, which transfers clean water to a clean water tank, the internal deviator being provided with a first deviation outlet and a second deviation outlet, both being downwardly oriented in a default position in which the first deviation outlet is aligned with the turbid water outlet, and the second deviation outlet is blocked, the internal deviator being able to turn within the external body, driven by the actuating device; and
a control module provided with a data bank containing information on the correlation of water turbidity and light absorption for the source of light being used, wherein:

the control module receives signals from the water passage sensor in order to command the light beam emitter;

the control module also receives signals from the light beam sensor in order to command the actuating device; and a signalization panel is provided to the control module to indicate the status of the whole operation of the apparatus to classify and separate turbid water and clean water.

2. The apparatus of claim 1 further including an air bubbles release device installed upstream of the first downward pipe of the first descending/ascending pipage.

3. The apparatus of claim 2 further including first and second air vents installed in the turbidity metering section near the first and second ends, respectively.

4. The apparatus of claim 3 further including a heating system provided in said first and second windows.

5. The apparatus of claim 4 further including first and second drains, located upstream of and downstream of the turbidity metering section, respectively, provided with first and second blocking valves, respectively.

6. The apparatus of claim 5 further including a chlorinator provided in the clean water transfer pipe and located upstream of the clean water tank.

7. The apparatus of claim 6 further including a level sensor installed in the clean water tank to sense high level of clean water and to send a signal to the control module, which sends a command signal to a draining device which discards the excess of water in the clean water tank via a releasing outlet.

8. The apparatus of claim 7 further including an acoustic device which emits sound signals when receiving signals from the control module informing that at least one component is malfunctioning.

9. The apparatus of claim 8 further including a no-break device provided with an internal rechargeable battery.

10. The apparatus of claim 9 further including a third blocking valve provided in the feeding pipe and installed downstream of a discarding deviation, the latter being provided with a fourth blocking valve.

11. The apparatus of claim 9 further including a receiving reservoir to receive said turbid water and clean water coming from a collecting source via a supply pipe, the receiving reservoir being provided with a receiving reservoir air vent and a receiving reservoir outlet, which is connected to the feeding pipe.

12. The apparatus of claim 11 further including a third blocking valve provided in the supply pipe and installed downstream of a discarding deviation, the later being provided with a fourth blocking valve.

13. A method to classify and separate turbid water and clean water in an flow of water comprising the steps of:

allow said flow of water to pass through a feeding pipe;

allow a water passage sensor to sense the passage of said flow of water in the feeding pipe and to send a signal to a control module informing the passage of said flow of water;

allow the control module to send a command signal to a light beam emitter located in front of a first transparent window of a turbidity metering section to start beaming light;

next allow the flow of water to enter a first descending/ascending pipage, flowing first through a first downward pipe, then through a first intermediate pipe and next through a first upward pipe;

allow the flow of water to pass through a turbidity metering section provided with first and second transparent windows located at opposite first and second ends of the turbidity metering section, said light beam emitter located in front of the first transparent window, and a light beam sensor located in front of the opposite second transparent window;

allow the light beam sensor located in front of the opposite second window to sense said beam of light and to send a signal to the control module;

next allow the flow of water to pass through a second descending/ascending pipage, flowing first through a second descending pipe, then through a second intermediate pipe and next through a second ascending pipe;

allow the flow of water to pass through a turbid water separation section comprising a deviation device provided with an actuating device, the deviation device comprising an external body, an internal deviator and an actuating device, the external body being provided with a turbid water outlet connected to a discard outlet, and a clean water outlet connected to a clean water transfer pipe, the internal deviator being provided with a first deviation outlet and a second deviation outlet, both being downwardly oriented in a default position, in which the first deviation outlet is aligned with the turbid water outlet, and the second deviation outlet is blocked, the internal deviator being able to turn within the external body, driven by the actuating device;

allow the initial flow of water to flow through the first deviation outlet and through the turbid water outlet, to be discarded;

allow the control module to analyze and to automatically classify and separate the passing flow of water based on the signals received from the light beam sensor, accepting or rejecting the flow of water that do not match the desired standards;

whenever the control module decides that the flow of water meets the desired standards, then it sends a signal to the actuating device of the deviation device to rotate the internal deviator so as to enable the second deviation outlet to align with the clean water outlet, causing a flow of clean water to pass through the clean water transfer pipe towards a clean water tank.

14. The method of claim 13 in that the signals received from the water passage sensor are also considered in the step wherein the control module analyzes and automatically classifies and separates the passing flow of water based on the signals received from the light beam sensor.

15. The method of claim 14 further comprising a step of chlorinating the flow of clean water in a chlorinator before it is directed to said clean water tank.

16. The method of claim 15 further comprising a step of sensing a high level of clean water in the clean water tank, via a level sensor, which sends a signal to the control module, which in turn makes a draining device to discard the excess of clear water via a releasing outlet.

17. The method of claim 16 further comprising the step of the control module sending a command signal to a third blocking valve provided in one among the supply pipe and the feeding pipe to shut off, and also sending a command signal to a fourth blocking valve to open, said fourth blocking valve installed in a discarding deviation located upstream of said third blocking valve, thereby making the flow of said flow of water to be discarded, the control module also sending a command signal to the light beam emitter to stop emitting light signals.

18. The method of claim 17 further comprising the step of allowing the level sensor to keep sensing the level of clean water into the clean water tank and whenever it senses that said level reduces to a pre-established level, then the level sensor sends a signal to the control module, which sends a command signal to the draining device to close and also sends a command signal to the third blocking valve to open and to the fourth blocking valve to shut off, and further the command module sends a command signal to the light beam emitter to send again light signals to the light beam sensor.

* * * * *